(12) United States Patent
Lenka et al.

(10) Patent No.: US 9,595,097 B1
(45) Date of Patent: Mar. 14, 2017

(54) SYSTEM AND METHOD FOR MONITORING LIFE OF AUTOMOBILE OIL (71) Applicant: Wipro Limited, Bangalore (IN)

(72) Inventors: Anil Kumar Lenka, Bangalore (IN); Raghavendra Hosabettu, Bangalore (IN)

(73) Assignee: WIPRO LIMITED, Bangalore (IN)

( * ) Notice: Subject to any disclaimer, the term of this patent is extended or adjusted under 35 U.S.C. 154(b) by 0 days.

(21) Appl. No.: 15/084,120

(22) Filed: Mar. 29, 2016

(30) Foreign Application Priority Data

Feb. 15, 2016 (IN) .............................. 201641005253

(51) Int. Cl.
*G06T 7/00* (2006.01)
*G07C 5/00* (2006.01)
*G07C 5/08* (2006.01)
*G01N 33/28* (2006.01)
*G01N 21/94* (2006.01)
*G01N 21/88* (2006.01)

(52) U.S. Cl.
CPC ......... *G06T 7/001* (2013.01); *G01N 21/8851* (2013.01); *G01N 21/94* (2013.01); *G01N 33/2835* (2013.01); *G01N 33/2888* (2013.01); *G06T 7/0008* (2013.01); *G07C 5/008* (2013.01); *G07C 5/085* (2013.01); *G01N 2021/889* (2013.01); *G06T 2207/10016* (2013.01); *G06T 2207/30108* (2013.01)

(58) Field of Classification Search
CPC .................... G06T 7/001; G06T 7/0008; G06T 2207/10016; G06T 2207/30108; G01N 21/8851; G01N 21/94; G01N 33/2835; G01N 33/2888; G01N 2021/889; G07C 5/008; G07C 5/085
USPC ........................................................ 701/31.4
See application file for complete search history.

(56) References Cited

U.S. PATENT DOCUMENTS

| | | | |
|---|---|---|---|
| 5,331,156 A * | 7/1994 | Hines .................... | G01N 21/359 250/256 |
| 2008/0204749 A1* | 8/2008 | Haddock ............ | G01N 15/0205 356/335 |
| 2012/0007979 A1* | 1/2012 | Schneider ................. | G01J 3/36 348/116 |
| 2016/0024915 A1* | 1/2016 | Duchene ................. | E21B 47/06 166/305.1 |
| 2016/0024916 A1* | 1/2016 | de Oliveira ............. | E21B 37/06 166/264 |

* cited by examiner

*Primary Examiner* — McDieunel Marc
*Assistant Examiner* — James E Stroud
(74) *Attorney, Agent, or Firm* — Finnegan, Henderson, Farabow, Garrett & Dunner, LLP (57) ABSTRACT

The present disclosure discloses a method and a device for monitoring life of automobile oil. The method comprising, receiving, by an oil life indication device, a video from an imaging unit communicatively coupled to the oil life indication device, where the video displays spreading of the automobile oil over a slope surface. The method comprises extracting a plurality of image frames from the video, determining one or more parameter values for at least one quality factors of the automobile oil and comparing the one or more parameter values with predefined threshold values to estimate life of the automobile oil.

15 Claims, 5 Drawing Sheets

SYSTEM AND METHOD FOR MONITORING LIFE OF AUTOMOBILE OIL

TECHNICAL FIELD

The present disclosure relates generally to a method for monitoring life of a fluid. In particular, the present disclosure relates to a method and an oil life indication device for monitoring life of automobile oil using image processing techniques.

BACKGROUND

It is known that various machines need fluid to operate smoothly. One such machine being an automobile, which needs engine oil for proper working of the engine. The role of engine oil is to keep the moving parts of the engine lubricated, to protect them against friction, rust and corrosion. Hence, it is required to change automobile engine oil at right time to keep the functioning as well as health of the automobile in good condition. Over time during usage, the engine oil breaks down, leading to change in the colour of the oil.

Normally, the service manual of automobile specifies the schedule and period for changing the oil depending upon usage. The oil change schedule is mostly synchronized with the normal service schedule of the automobile which, in most cases, is based on either usage or the duration from latest service. Sometimes, during servicing of an automobile, it has been found that the oil change is not necessary despite being recommended as per the service manual. Hence, a user may conclude that is not always necessary to change the oil every time the automobile is serviced. At times, even if the colour and texture of the oil may be deceiving. Thus, a change in colour may not always mean that the oil life has expired.

In such a situation, the user always faces a dilemma whether to change the oil as recommended in the normal service manual or skip changing the oil. If at all a decision to not change the oil is taken, the user cannot be accurate and certain about the decision taken.

SUMMARY

The present disclosure presents a method and an oil life indication device for monitoring life of automobile oil by applying image processing techniques on plurality of images of the automobile oil received from an imaging unit.

In one embodiment, the present disclosure discloses a method for monitoring life of automobile oil. The method comprising, receiving, by an oil life indication device, a video from an imaging unit communicatively coupled to the oil life indication device, where the video displays spreading of the automobile oil over a slope surface, extracting a plurality of image frames from the video, determining one or more parameter values for at least one quality factors of the automobile oil and comparing the one or more parameter values with predefined threshold values to estimate life of the automobile oil.

In an embodiment, the present disclosure presents an oil life indication device for monitoring life of automobile oil, comprising, a processor and a memory communicatively coupled to the processor. Here, the processor is configured to receive a video from an imaging unit communicatively coupled to the oil life indication device, where the video displays spreading of the automobile oil over a slope surface, extract a plurality of image frames from the video, determine one or more parameter values for at least one quality factors of the automobile oil and compare the one or more parameter values with predefined threshold values to estimate life of the automobile oil.

In another embodiment, the present disclosure relates to a non-transitory computer readable medium including instructions stored thereon that when processed by at least one processor causes a monitoring device to perform the act of receiving a video from an imaging unit communicatively coupled to the oil life indication device, where the video displays spreading of the automobile oil over a slope surface, extracting a plurality of image frames from the video, determining one or more parameter values for at least one quality factors of the automobile oil and comparing the one or more parameter values with predefined threshold values to estimate life of the automobile oil.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternatives falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure relate to a method and an oil life indication device for monitoring life of automobile oil. The oil life indication device applies image processing techniques on plurality of images of the automobile oil to extract certain features of the oil. Then, the extracted features are compared with predefined parameters to estimate life of the automobile oil. Further, the estimation is monitored and notified to a user, thereby indicating when to change the oil.

Figure 1:
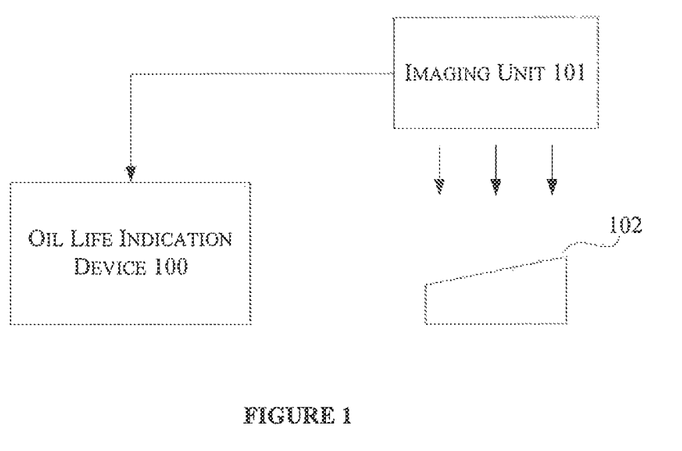
FIG. 1 illustrates a block diagram of an oil life indication device associated with an imaging unit to monitor life of automobile oil in accordance with some embodiments of the present disclosure.

In an embodiment, the present disclosure presents an oil life indication device for monitoring life of automobile oil. FIG. 1 of the present disclosure shows a block diagram of an oil life indication device 100 communicatively coupled with an imaging unit 101, to estimate life of automobile oil herein referred to as oil. As shown in FIG. 1, the oil is dropped on a surface 102 positioned at a predefined angle to form a slope. The imaging unit 101 captures a video of the oil as it spreads over the surface 102. In one embodiment, the imaging unit 101 may be connected to the oil life indication device 100 either through wired interface or wireless interface. In an embodiment, the imaging unit 101 may be integrated into the oil life indication device 100. Further, the oil life indication device 100 receives the captured video and estimates life of the oil by analyzing one or more quality factors of the oil. In an exemplary embodiment, a user may drop a predefined amount of oil over the surface 102. In an embodiment, the surface 102 may be a smooth surface 102 enabling uniform spreading of the oil. For example, the surface 102 may include, but is not limited to, a glass surface 102, a metal surface 102, a wooden surface 102, etc.

Figure 2:
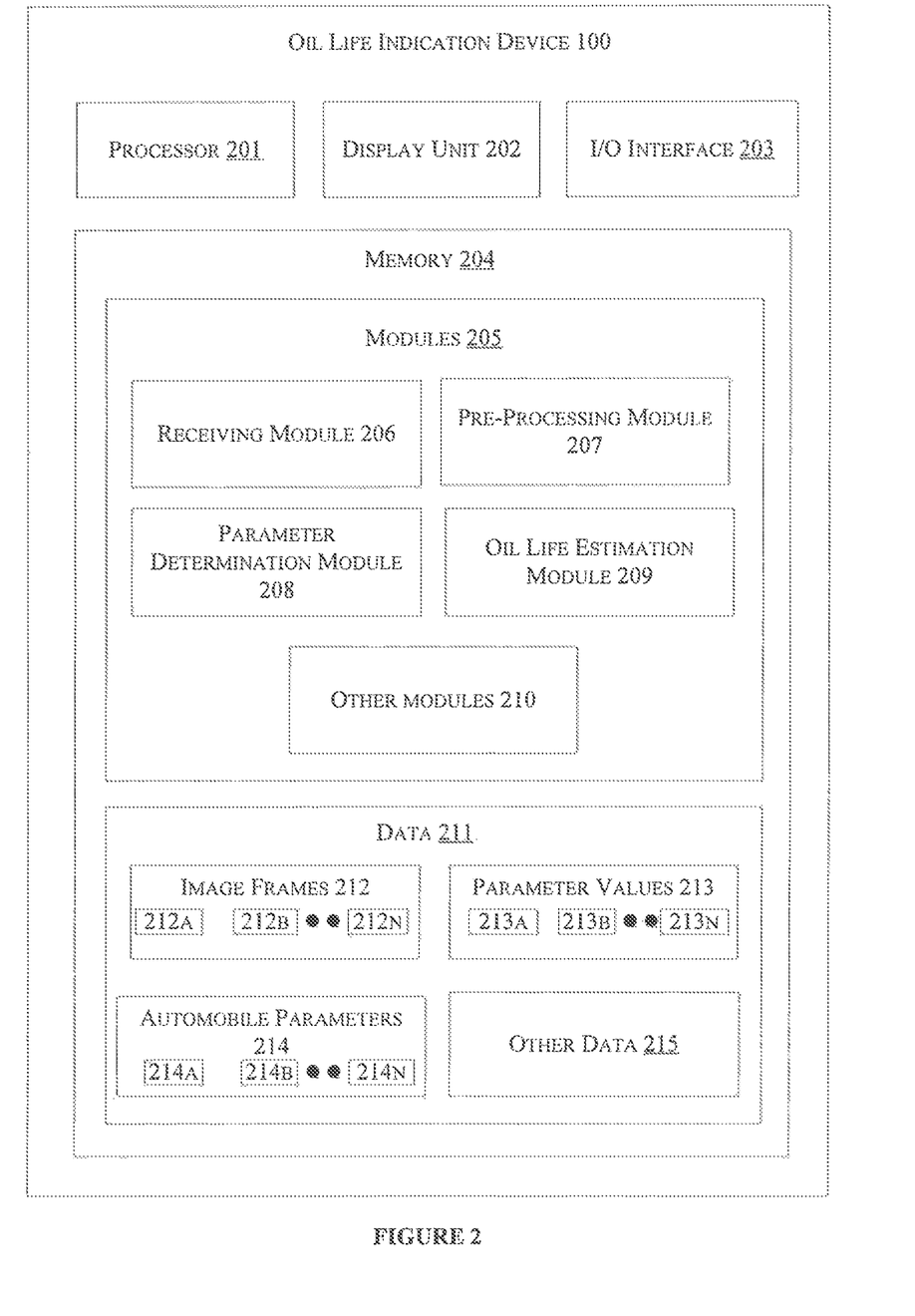
FIG. 2 shows an exemplary block diagram of internal architecture of an oil life indication device to monitor life of automobile oil in accordance with some embodiments of the present disclosure.

FIG. 2 of the present disclosure shows an exemplary block diagram of internal architecture of the oil life indication device 100 to estimate and monitor life of the oil. The oil life indication device 100 may include at least one central processing unit ("CPU" or "processor") 201 and a memory 204 storing instructions executable by the at least one processor 201. The processor 201 may comprise at least one data processor 201 for executing program components for executing user or system-generated requests. A user may include a person, a person using a device such as those included in this disclosure, or such a device itself. The memory 204 is communicatively coupled to the processor 201. In an embodiment, the memory 204 stores one or more data 210. The oil life indication device 100 further comprises an Input/Output (I/O) interface 203. The I/O interface 203 is coupled with the processor 201 through which an input signal or/and an output signal is communicated. The oil life indication device 100 may also comprise a display unit 202 to display the estimated life of the oil.

In an embodiment, one or more data 210 may be stored within the memory 204. The one or more data 210 may include, for example, image frames, parameter values, automobile parameters and other data 215. Image frames 212A, image frames 212B, . . . , image frames 212N may be collectively represented as plurality of image frames 212. Parameter values 213A, Parameter values 213B, . . . , Parameter values 213N may be collectively represented as one or more Parameter values 213. The processor 201 estimates life of the oil based on the one or more parameter values. Automobile parameters 214A, automobile parameters 214B, . . . , automobile parameters 214N may be collectively represented as one or more automobile parameters 214. Also, the one or more data 210 may comprise other data 215. The other data 215 may be used to store data, including temporary data and temporary files, generated by modules 205 for performing various functions of oil life indication device 100.

In an embodiment, the one or more quality factors of the oil may include, but are not limited to, colour, dust particles, dust particles density, size of the dust particles, viscosity, and velocity of the flow of the automobile oil. In an embodiment, the one or more quality factors 211 may also include other parameters pertaining to the automobile oil.

In an embodiment, the one or more automobile parameters 214 may include, but are not limited to type of oil, type of automobile, amount of usage of the automobile and type of terrain the automobile is used. In an embodiment, the automobile parameters 214 may also include other parameters pertaining to the automobile.

In an embodiment, the one or more data 210 in the memory 204 is processed by modules 205 of the oil life indication device 100. The modules 205 may be stored within the memory 204. In an example, the modules 205, communicatively coupled with the processor 201, may also be present outside the memory 204. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

In one implementation, the modules may include, for example, a receiving module 206, a pre-processing module 207, a parameter determination module 208, an oil life estimation module 209 and other modules 210. It will be appreciated that such aforementioned modules may be represented as a single module or a combination of different modules.

In an embodiment, the receiving module 206 receives one or more user inputs. The one or more user inputs are at least one of, type of oil, type of automobile, amount of usage of the automobile and type of terrain the automobile is used. Further, the one or more user inputs are selected from the one or more automobile parameters 214 stored in the database. Further, the one or more user inputs are received by the oil life identification device 100 through the I/O interface 203. Further, the receiving module 206 receives the video captured by the imaging unit 101.

In an embodiment, the pre-processing module 207 receives the video from the receiving module 206. Then, the pre-processing module 207 extracts plurality of image frames 212 of the oil with respect to time using image processing techniques. Further, the pre-processing module 207 processes the plurality of image frames 212, which are used for estimating life of the oil. The processing of the plurality of image frames 212 may include, but are not limited to image enhancement, contrast and brightness normalization, rotation alignment, scale adjustment, segmentation, etc.

In one embodiment, the parameter determination module 208, receives the plurality image frames 212 from the pre-processing module 208. The parameter determination module 208 determines corresponding one or more parameter values 213 for each of the one or more quality factors of the oil. The one or more quality factors of the oil may be, but are not limited to colour, dust particles, dust particles density, size of the dust particles, viscosity, and velocity of the flow of the automobile oil. In one embodiment, the parameter determination module 208 may apply various image processing techniques on the plurality of image frames 212 to determine the one or more parameter values 213.

In an embodiment, the oil life estimation module 209 receives the one or more parameter values from the parameter determination module 208. Further, the oil life estimation module 209 compares the one or more parameters values with corresponding predefined one or more parameter values based on the one or more user inputs.

In an embodiment, the predefined one or more parameter values may be stored in the database. In an embodiment, the predefined one or more parameter values are threshold values corresponding to the one or more quality factors. The predefined one or more parameter values may also be referred as predefined one or more threshold values. Further, the oil life estimation module 209 determines a final value from the comparison, using machine learning algorithms. Upon comparing the final value with a predefined final value, the oil life estimation module 209 estimates life of the oil.

In an embodiment, the oil life indication device 100 displays the estimated oil life to the user using the display unit 202. In an exemplary embodiment, the oil life indication device 100 monitors the life of the oil and indicates the user the life of the oil at predefined intervals. In an embodiment, the oil life indication device 100 may be integrated with an automobile to continuously estimate and monitor life of the automobile oil in real-time.

In an embodiment, the memory 204 may also comprise other data 215 related to the oil for estimating and monitoring the life of the oil. In an embodiment, the memory 204 may also comprise other modules 210 to perform tasks for estimating and monitoring life of the oil.

Figure 3:
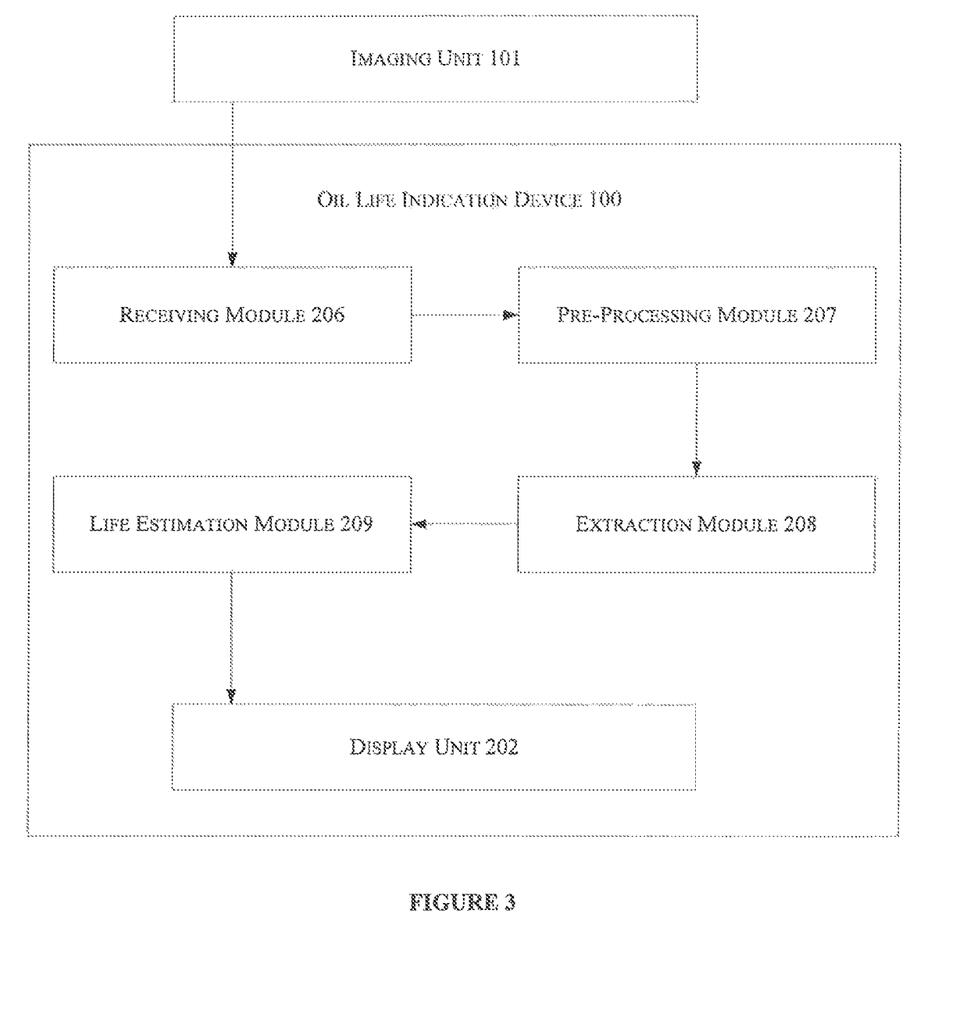
FIG. 3 shows a system illustrating process flow for monitoring life of automobile oil in accordance with some embodiments of the present disclosure.

FIG. 3 of the present disclosure shows a system illustrating process flow for monitoring life of automobile oil.

Figure 4:
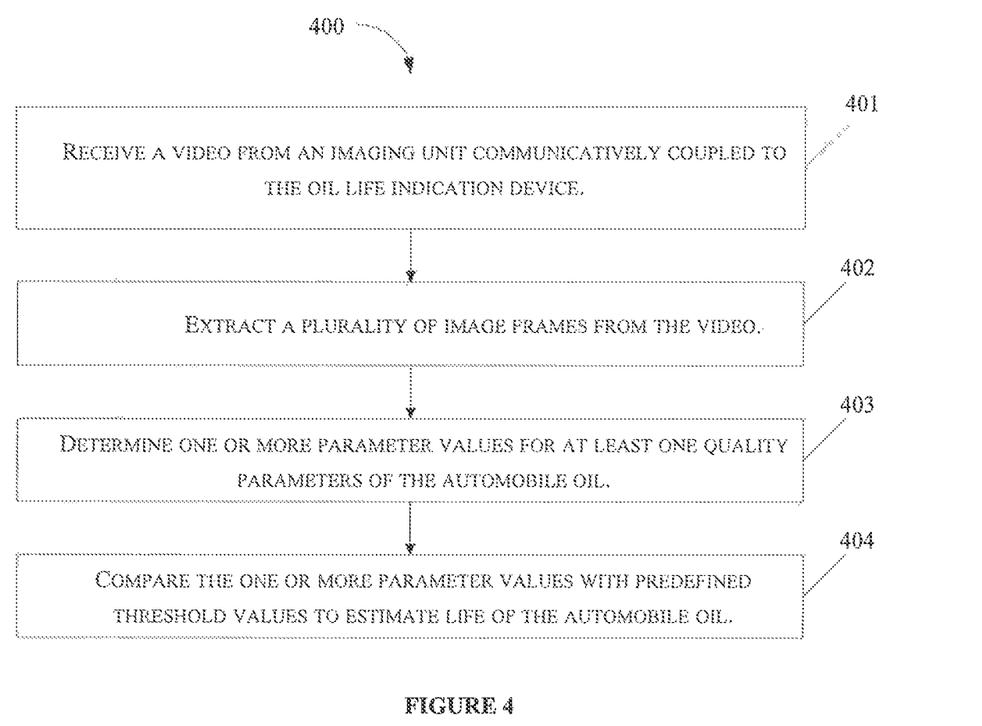
FIG. 4 shows a flow chart illustrating a method for monitoring life of automobile oil in accordance with some embodiments of the present disclosure.

FIG. 4 shows a flowchart illustrating a method for monitoring life of automobile oil in accordance with some embodiments of the present disclosure.

As illustrated in FIG. 4, the method 400 may comprise one or more steps to estimate and monitor life of an automobile oil. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At step 401, receive, by the oil life indication device 100, a video from the imaging unit 101 communicatively coupled to the oil life indication device 100. Here, the imaging unit 101 captures a video of the oil spreading over the surface 102. The oil life indication device 100 receives the captured video from the imaging unit 101 to estimate and monitor life of the oil. In an embodiment, the oil life indication device 100 may receive the video from the imaging unit 101 through wired interface or wireless interface.

In an embodiment, the surface 102 is placed at a predefined angle to form a slope. The surface 102 is inclined at the predefined angle for enabling the oil to spread at a uniform rate over the surface 102. In an embodiment, the user may drop the oil on the surface 102.

At step 402, extracting by the pre-processing module 207, a plurality of image frames 212 from the video. The oil life indication device 100 extracts a plurality of image frames 212 from the received video from the imaging unit 101 communicatively coupled with the oil life indication device 100. Here, the plurality of image frames 212 are extracted with respect to time, i.e. each of the plurality of image frames 212 shows spreading of the oil over the surface 102 at a predefined unit of time. The plurality of image frames 212 are used to determine the one or more parameter values 213 corresponding to the one or more quality factors of the oil.

At step 403, determining, by the parameter determination module 208, one or more parameter values 213 corresponding to the one or more quality factors, from the plurality of image frames 212. The oil life indication device 100 uses image processing techniques to determine the one or more parameter values 213. Further, the oil life indication device 100 estimates and monitors life of the oil based on the one or more parameter values.

At step 404, comparing, by the oil life estimation module 209 the one or more parameter values with predefined one or more threshold values to estimate life of the oil. Each of the predefined one or more threshold values correspond to respective one or more quality factors. The oil life indication device 100 compares the determined parameter values with the corresponding predefined one or more threshold values based on the one or more user inputs. Further, the oil life indication device 100 determines a final value from the comparison, using machine learning algorithms. Upon comparing the final value with a predefined final value, the oil life indication device 100 estimates life of the oil.

In one embodiment, consider an example of estimating life of the oil with the data as represented in table 1. The data shown in table 1 are stored in the database. The data shown in table 1 are considered for few quality factors and automobile parameters.

TABLE 1

| AUTOMOBILE TYPE | AUTOMOBILE PARAMETERS | THESHOLD VALUES | FINAL VALUE |
|---|---|---|---|
| Vehicle 1 | Oil 1 | 0.926 | 0.295 |
| | Oil 2 | 0.955 | 0.327 |
| Vehicle 2 | Oil 1 | 0.891 | 0.513 |
| | Oil 2 | 0.913 | 0.536 |

From Table 1, the types of automobile are Vehicle 1 and vehicle 2. The type of oil is oil 1 and oil 2. From the data as shown in Table 1, the user selects the automobile type and automobile parameters 214. In one instance, let the user select automobile type as Vehicle 1 and oil 1 as the oil type. The oil life indication device 100 begins the method for estimating life of the oil with receiving a video of the oil 1 spreading over the surface 102. Further the oil life indication device 100 extracts plurality of image frames 212 from the video. Furthermore, the oil life indication device 100 determines the one or more parameter values 213 corresponding to the one or more quality factors, from the extracted plurality of image frames 212. The determined parameter values are then compared with threshold values corresponding to the selected user inputs. From the table, the threshold value for the selected user inputs is 0.926. The determined parameter value is compared with the threshold value 0.926. Further, the oil life indication device 100 determines a final value based on the comparison made. The determined final value is then compared with a predefined final value to estimate life of the oil. From the table, the predefined final value for the selected user inputs is 0.295. The oil life indication device 100 compares the determined final value with predefined final value 0295 and estimates the oil life using machine algorithm.

In an embodiment, the oil life indication device 100 can be used to identify life of any fluid compatible with the requiring the method steps as described in this disclosure. In an embodiment, the oil life indication device 100 stores the estimated oil life data and the determined parameters for the one or more user inputs in the database. The machine learning algorithm uses the stored data for subsequent estimation for similar type of data, thus increasing the accuracy of estimation.

In an embodiment, a method for extracting the one or more image frames is disclosed herein. Firstly, the oil is dropped in the centre of the surface 102 and a video of the oil spreading over the surface 102 is captured by the imaging unit 101. Then, the pre-processing module 207 extracts individual image frames from the video to generate a sequence of predefined image format. Here, the pre-processing module 207 extracts an image frame at a predefined time interval to receive plurality of image frames 212. In one embodiment, the image formats can be, but is not limited to, Joint Photographic Experts Group (JPEG), Portable Network Graphics (PNG) and Bit Map (BMP). The extracted plurality of image frames 212 are used to determine one or more parameter values corresponding to the one or more quality factors. The oil life indication device 100 estimates the oil life based on the one or more parameter values 213.

In an embodiment, a method for determining parameter values 213 for based on colour of the oil is disclosed. In an example, the present disclosure uses Blob detection methods to determined parameter values 213 based on colour of the oil. The method comprises detecting regions in the image that differ in properties, such as brightness or colour, compared to surrounding regions. Blob is a region of an image in which some properties are constant or approximately constant. Further, the method comprises converting the captured colour image to the predefined format thereby easing the colours to separate. Further, the image is split into components for determining the parameter values 213.

Computer System

Figure 5:
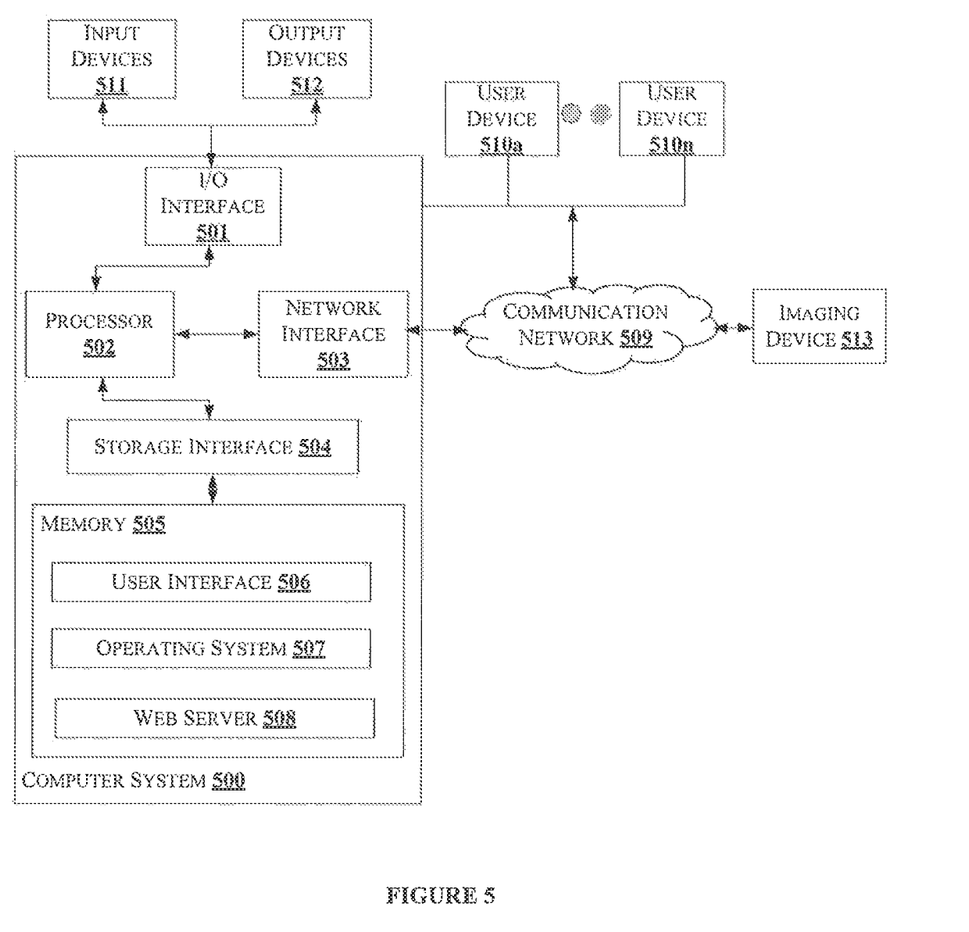
FIG. 5 is a block diagram of an exemplary computer system for implementing embodiments consistent with the present disclosure.

FIG. 5 illustrates a block diagram of an exemplary computer system 500 for implementing embodiments consistent with the present disclosure. In an embodiment, the computer system 500 is used to implement the method for monitoring life of automobile oil. The computer system 500 may comprise a central processing unit ("CPU" or "processor") 502. The processor 502 may comprise at least one data processor for executing program components for dynamic resource allocation at run time. The processor 502 may include specialized processing units such as integrated system (bus) controllers, memory management control units, floating point units, graphics processing units, digital signal processing units, etc.

The processor 502 may be disposed in communication with one or more input/output (I/O) devices (not shown) via I/O interface 501. The I/O interface 501 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 501, the computer system 500 may communicate with one or more I/O devices. For example, the input device 511 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device 512 may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 500 is connected to the service operator through a communication network 509. The processor 502 may be disposed in communication with the communication network 509 via a network interface 503. The network interface 503 may communicate with the communication network 509. The network interface 503 may employ connection protocols including, without limitation, direct connect, Ethernet (e.g., twisted pair 10/100/1000 Base T), transmission control protocol/Internet protocol (TCP/IP), token ring, IEEE 802.11a/b/g/n/x, etc. The communication network 509 may include, without limitation, a direct interconnection, e-commerce network, a peer to peer (P2P) network, local area network (LAN), wide area network (WAN), wireless network (e.g., using Wireless Application Protocol), the Internet, Wi-Fi, etc. Using the network interface 503 and the communication network 509, the computer system 500 may communicate with the one or more service operators.

In some embodiments, the processor 502 may be disposed in communication with a memory 505 (e.g., RAM, ROM, etc. not shown in FIG. 5) via a storage interface 504. The storage interface 504 may connect to memory 505 including, without limitation, memory drives, removable disc drives, etc., employing connection protocols such as serial advanced technology attachment (SATA), Integrated Drive Electronics (IDE), IEEE-1394, Universal Serial Bus (USB), fibre channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 505 may store a collection of program or database components, including, without limitation, user interface 506, an operating system 507, web server 508 etc. In some embodiments, computer system 500 may store user/application data 506, such as the data, variables, records, etc. as described in this disclosure. Such databases may be implemented as fault-tolerant, relational, scalable, secure databases such as Oracle or Sybase.

The operating system 507 may facilitate resource management and operation of the computer system 500. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, 10 etc.), Apple iOS, Google Android, Blackberry OS, or the like.

In some embodiments, the computer system 500 may implement a web browser 507 stored program component. The web browser 508 may be a hypertext viewing application, such as Microsoft Internet Explorer, Google Chrome, Mozilla Firefox, Apple Safari, etc. Secure web browsing may be provided using Secure Hypertext Transport Protocol (HTTPS), Secure Sockets Layer (SSL), Transport Layer Security (TLS), etc. Web browsers 508 may utilize facilities such as AJAX, DHTML, Adobe Flash, JavaScript, Java, Application Programming Interfaces (APIs), etc. In some embodiments, the computer system 500 may implement a mail server stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 500 may implement a mail client stored program component. The mail client may be a mail viewing application, such as Apple Mail, Microsoft Entourage, Microsoft Outlook, Mozilla Thunderbird, etc.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise. The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise. The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Technical Advantages of the Present Invention

In an embodiment, the present disclosure notifies a user an estimation of oil life, thus indicating the user when to change the oil.

In an embodiment, the present disclosure describes a method for continuously monitoring life of the oil. The monitored oil life may be notified to the user in real time, for predefined automobile parameters.

In an embodiment, the oil life indication device is portable and can be carried anywhere. Further, the oil life indication device can have a built-in imaging unit or associated with external imaging unit.

In an embodiment, the accuracy of estimating the oil life increases as the method in the present disclosure employs machine learning algorithm.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference number | Description |
| --- | --- |
| 100 | Oil life indication device |
| 101 | Imaging unit |
| 102 | Surface |
| 201 | Processor |
| 202 | Display unit |
| 203 | I/O interface |
| 204 | Memory |
| 205 | Modules |
| 206 | Receiving module |
| 207 | Pre-processing module |
| 208 | Parameter determination module |
| 209 | Oil life estimation module |
| 210 | Other modules |
| 211 | Data |
| 212 | Image frames |
| 213 | Parameter values |
| 214 | Automobile parameters |
| 215 | Other data |
| 500 | General computer system |
| 501 | I/O Interface |
| 502 | Processor |
| 503 | Network Interface |
| 504 | Storage Interface |
| 505 | Memory |
| 506 | User Interface |
| 507 | Operating System |
| 508 | Web Server |
| 509 | Communication Network |
| 510 | User device |
| 511 | Input Device |
| 512 | Output Device |
| 513 | Imaging device |

We claim:

1. A method of monitoring life of automobile oil, comprising:
receiving, by an oil life indication device via a processor, a video from an imaging unit communicatively coupled to the oil life indication device, wherein the video displays spreading of the automobile oil over a slope surface;
extracting, by the oil life indication device via the processor, a plurality of image frames from the video;
determining, by the oil life indication device via the processor, one or more parameter values for at least one quality factors of the automobile oil; and
comparing, by the oil life indication device via the processor, the one or more parameter values with predefined threshold values to estimate life of the automobile oil.

2. The method as claimed in claim 1, wherein the one or more quality factors comprises at least one of colour, dust particles, dust particles density, size of the dust particles, viscosity, and velocity of the flow of the automobile oil.

3. The method as claimed in claim 1, wherein the predefined threshold values are determined based on user inputs and one or more predefined automobile parameters stored in a database accessible by the oil life indication device.

4. The method as claimed in claim 1, wherein, for each of the predefined automobile parameters, the one or more parameters of the oil with corresponding threshold values are stored in the database.

5. The method as claimed in claim 4, wherein the one or more inputs are at least one of, type of oil, type of automobile, amount of usage of the automobile and type of terrain the automobile is used.

6. An oil life indication device for monitoring life of automobile oil, comprising:
a processor; and
a memory communicatively coupled to the processor, wherein the memory stores processor-executable instructions, which, on execution, causes the processor to:
receive a video from an imaging unit communicatively coupled to the oil life indication device, wherein the video displays spreading of the automobile oil over a slope surface;
extract a plurality of image frames from the video;
determine one or more parameter values for at least one quality factors of the automobile oil; and
compare the one or more parameter values with predefined threshold values to estimate life of the automobile oil.

7. The oil life indication device as claimed in claim 6, wherein the one or more quality factors comprises at least one of colour, dust particles, dust particles density, size of the dust particles, viscosity, and velocity of the flow of the automobile oil.

8. The oil life indication device as claimed in claim 6, wherein the predefined threshold values are determined based on user inputs and one or more predefined automobile parameters stored in a database accessible by the oil life indication device.

9. The oil life indication device as claimed in claim 8, wherein, for each of the predefined automobile parameters, the one or more parameters of the oil with corresponding threshold values are stored in the database.

10. The oil life indication device as claimed in claim 7, wherein the one or more inputs are at least one of, type of oil, type of automobile, amount of usage of the automobile and type of terrain the automobile is used.

11. A non-transitory computer readable medium including instructions stored thereon that when processed by at least one processor cause a device to perform operations comprising:
receiving a video from an imaging unit communicatively coupled to the oil life indication device, wherein the video displays spreading of the automobile oil over a slope surface;
extracting a plurality of image frames from the video;
determining one or more parameter values for at least one quality factors of the automobile oil; and comparing the one or more parameter values with predefined threshold values to estimate life of the automobile oil.

12. The medium as claimed in claim 11, wherein the one or more quality factors comprises at least one of colour, dust particles, dust particles density, size of the dust particles, viscosity, and velocity of the flow of the automobile oil.

13. The medium as claimed in claim 11, wherein the predefined threshold values are determined based on user inputs and one or more predefined automobile parameters stored in a database accessible by the oil life indication device.

14. The medium as claimed in claim 13, wherein, for each of the predefined automobile parameters, the one or more parameters of the oil with corresponding threshold values are stored in the database.

15. The medium as claimed in claim 14, wherein the one or more inputs are at least one of, type of oil, type of automobile, amount of usage of the automobile and type of terrain the automobile is used.

* * * * *